United States Patent [19]

Berberich

[11] Patent Number: 5,600,254

[45] Date of Patent: Feb. 4, 1997

[54] PROCESS AND CIRCUIT ARRANGEMENT FOR MEASURING THE RESISTANCE OF A RESISTANCE SENSOR

[75] Inventor: Reinhold Berberich, Frankfurt, Germany

[73] Assignee: VDO Adolf Schindling AG, Frankfurt, Germany

[21] Appl. No.: 394,373

[22] Filed: Feb. 24, 1995

[30] Foreign Application Priority Data

Jun. 24, 1994 [DE] Germany .......................... 44 21 906.7

[51] Int. Cl.$^6$ .................................................. G01R 27/14
[52] U.S. Cl. ...................... 324/711; 324/712; 324/694; 324/678; 324/677; 318/DIG. 2
[58] Field of Search .......................... 324/444, 676, 324/677, 678, 710, 711, 712, 694; 318/DIG. 2

[56] References Cited

U.S. PATENT DOCUMENTS

| 3,495,164 | 2/1970 | Dauphinee | 324/710 |
| 3,757,205 | 9/1973 | Dauphinee | 324/710 |
| 4,786,875 | 11/1988 | Carll | 324/444 |
| 5,439,644 | 8/1995 | Gramkow | 324/444 |

FOREIGN PATENT DOCUMENTS

90/08680  8/1990  WIPO .

Primary Examiner—Kenneth A. Wieder
Assistant Examiner—Jose M. Solis
Attorney, Agent, or Firm—Martin A. Farber

[57] ABSTRACT

In a process and a circuit arrangement for measuring the resistance of a resistance sensor, for instance a wetness sensor, via a rate of change of the charge of a capacitor, a measurement cycle consisting in each case of a charging of a capacitor, a discharging of the capacitor over the resistance sensor, and thereupon a measurement of the charge remaining in the capacitor, the direction of the discharge current through the resistor changes from measurement cycle to measurement cycle.

10 Claims, 2 Drawing Sheets

PROCESS AND CIRCUIT ARRANGEMENT FOR MEASURING THE RESISTANCE OF A RESISTANCE SENSOR

FIELD AND BACKGROUND OF THE INVENTION

The present invention relates to a process and a circuit arrangement for measuring the resistance of a resistance sensor, particularly a wetness sensor, via the rate of change of the charge of a capacitor, one measurement cycle in each case consisting of a charging of the capacitor followed by an incomplete discharging of the capacitor over the resistance sensor, and then measurement of charge remaining in the capacitor.

As an example, in order to measure the wetness on the windshield of a motor vehicle, sensor resistors in the form of two strip-shaped electrodes which are interlaced in each other are used. If drops of water contact both electrodes, then the resistance decreases. The change in resistance is used for the automatic control of a windshield wiper. In order to measure the resistance, it is necessary, in principle, to apply a voltage to the resistance sensor. Due to dc-voltage portions of the voltage to be applied, electrolysis phenomena may however occur between the electrodes, leading finally to a decrease in the life of the resistance sensors. A device for controlling a drive means for an automobile accessory having such a resistance sensor is described, for instance, in WO 90/08680.

SUMMARY OF THE INVENTION

It is an object of the present invention to prevent electrolysis phenomena on resistance sensors, particularly wetness sensors.

According to the method of the invention, the direction of the discharge current through the resistance is varied from measurement cycle to measurement cycle.

The process of the invention has the advantage not only that electrolytic deposits on and corrosion of the electrodes are prevented, but also that the resistance to disturbing radiation is increased by the symmetric action on the resistance sensor.

The measurement of the charge which has remained in the capacitor can easily be effected in the manner that the capacitor is discharged further by a defined amount and that the time of the defined discharge until a reduction of voltage below a predetermined amount is measured, or that the capacitor is again charged by a defined amount and the time of the defined charging until a predetermined voltage is exceeded is measured.

A further development of the process of the invention provides that the circuit formed with the resistance sensor for the discharge of the capacitor is free of potential. Due to the fact that, in this further development, the resistance sensor and the capacitor are not acted on either by ground potential or by a potential differing therefrom, no currents are formed between the electrodes of the resistance sensor and the body of the car, so that electrolysis caused by such currents is also prevented.

One advantageous embodiment of the process of the invention provides that, from measurement cycle to measurement cycle, the capacitor is connected with alternating polarity to a source of charge/discharge current and to an input of a threshold circuit.

The invention furthermore comprises an advantageous circuit arrangement for the carrying out of the process wherein a source of charge/discharge current (20, 21, 22), the input (14) of a threshold circuit (15 to 19), a resistance sensor (11) and a capacitor (8) are connected to a controllable two-pole multiple switch (multiplexer) (1), the multiplexer (1) connecting a pair of terminals (X; Y) with one of further pairs of terminals (X0 to X3; Y0 to Y3) as a function of control signals fed; that the pair of terminals (X; Y) is connected to the capacitor (8); that the resistance sensor (11) is connected to one (X3; Y3) of the further pairs of terminals; and that the input (14) of the threshold circuit (15 to 19) and ground potential are connected to a second one (X0; Y0) of the further pairs of terminals; and the input (14) of the threshold circuit (15 to 19) and ground potential are connected to a third one (X1; Y1) of the further pairs of terminals with polarity opposite that of the second (X0; Y0) further pair of terminals. Suitable multiplexers are available as integrated circuits on the market.

A particularly advantageous control of the multiplexer and of the source of charge/discharge current, as well as a measurement of the remaining charge by the counting of pulses until the charge voltage drops below a predetermined threshold, can be effected in simple fashion in the manner that control inputs of the multiplexer (1), the source of charge/discharge current (20 to 22), and an output of the threshold circuit (15 to 19) are connected to inputs and/or outputs of a microprocessor (2).

The multiplexers available on the market frequently have four additional pairs of terminals, so that a second resistance sensor can be easily connected.

The circuit arrangement of the invention can also be advantageously further developed in the manner that a fourth (X2; Y2) further pair of terminals can be connected to a reference resistor for purposes of self-calibration. In such case, the microcomputer contains a suitable program which uses the resistance measured in the case of the reference resistor for the measurement results in the case of the resistor sensor as comparison value.

BRIEF DESCRIPTION OF THE DRAWINGS

With the above and other objects and advantages in view, the present invention will become more clearly understood in connection with the detailed description of preferred embodiments, when considered with the accompanying drawings, of which.

DETAILED DESCRIPTION OF THE PREFERRED EMBODIMENT

Figure 1:
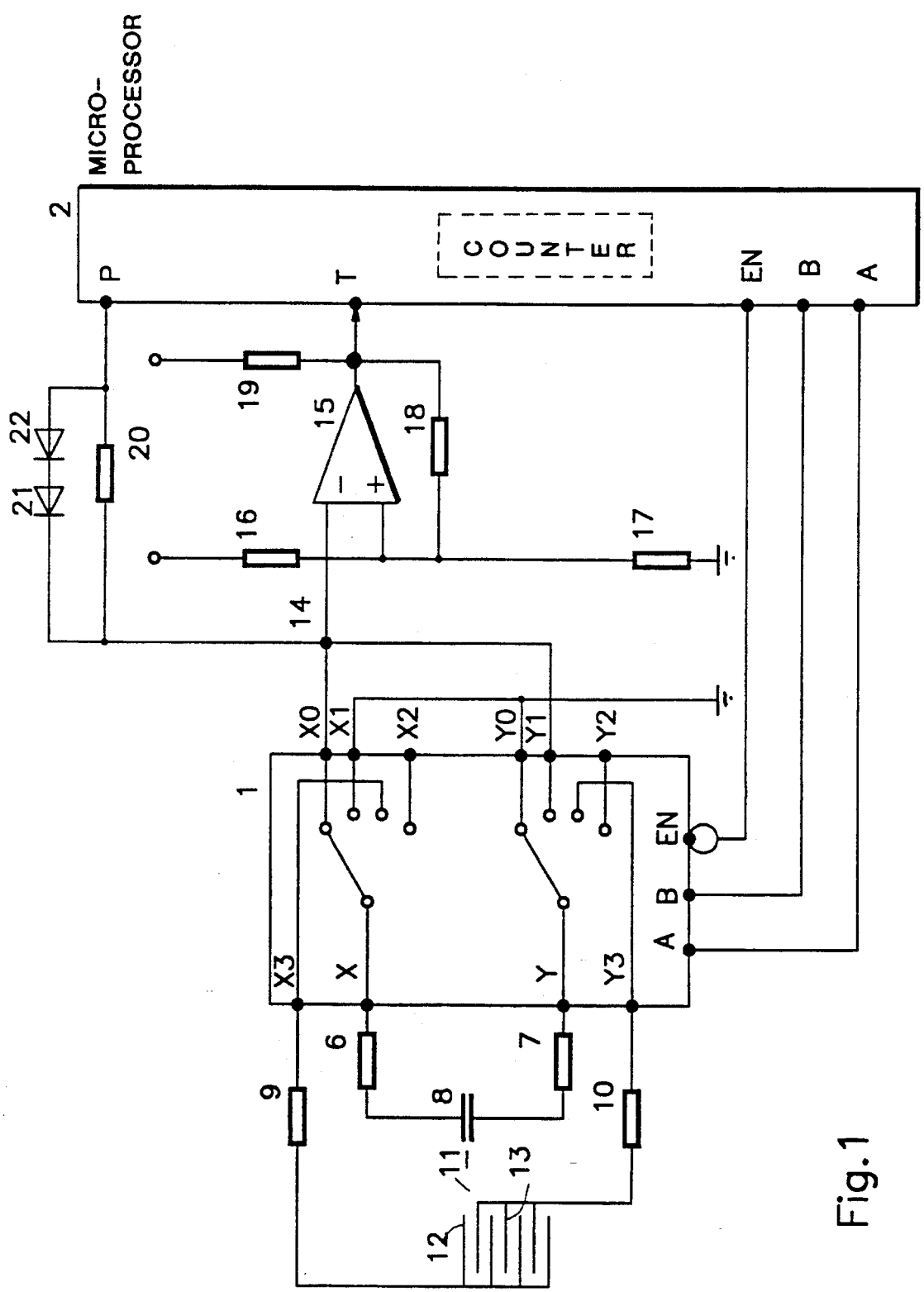
FIG. 1 is an electrical circuit according to the invention.

In the circuit arrangement shown in FIG. 1, the multiplexer 1 is a component available on the market, for instance of Type 4052, in which two input terminals X, Y can be connected, in each case, with one of further sets of output terminals X0, X1, X2 or X3, and/or Y0, Y1, Y2 or Y3 respectively as a function of control signals A, B which are applied to control terminals of the multiplexer 1. All possible connections can be made of high resistance by a further control signal EN. Although in such components the individual connections are switched via field-effect transistors, multiple switches are shown in FIG. 1 in order to make it clearer. The control signals A, B, EN are produced by a microprocessor 2 and fed to the control input terminals of the multiplexer 1.

The terminals X and Y of the multiplexer 1 are each connected via a resistor 6, 7 respectively to a capacitor 8. The resistors 6, 7 are intended to prevent peak currents upon the connecting of the capacitor 8. Protection against surge currents may be provided by the internal resistance which is anyhow present in the multiplexer 1. Via in each case a protective resistor 9, 10 there is connected to the terminals X3 and Y3 a resistance sensor 11 which consists of two interlaced comb-like electrodes 12, 13 which are applied, for instance, in the form of thin metal coatings onto the windshield of a motor vehicle. The protective resistors 9, 10 prevent damage to or destruction of the circuit of the invention in the event that battery voltage or ground potential might be applied to the resistance sensor which is located on the outside the circuitry of the multiplexer 1.

The terminals X0 and Y1 of the multiplexer are connected to an input 14 of a threshold circuit, while the terminals X1 and Y0 are connected to ground potential. The threshold circuit consists of a difference amplifier 15 to the noninverting input of which a bias voltage is fed via a voltage divider comprising resistors 16, 17. A part of the output voltage of the difference amplifier 15 is fed via a resistor 18 back to the noninverting input terminal of the amplifier 15. The inverting input of the amplifier is connected to the input 14 of the threshold circuit. The output of the difference amplifier 15 is connected with an input of the microprocessor 2 and, via a resistor 19, to positive operating voltage. The output voltage signal of the threshold circuit is designated T.

Another output of the microprocessor 2 provides a signal P which is used to form a charge current and a discharge current for the capacitor 8, and is connected to the input 14 of the threshold circuit via a measurement resistor 20 and two diodes 21, 22 which are connected in series along an electrical path in parallel with the resistor 20. The signals EN, B, A, P and T are binary signals, i.e they can assume in each case only one of two voltage levels.

Figure 2:
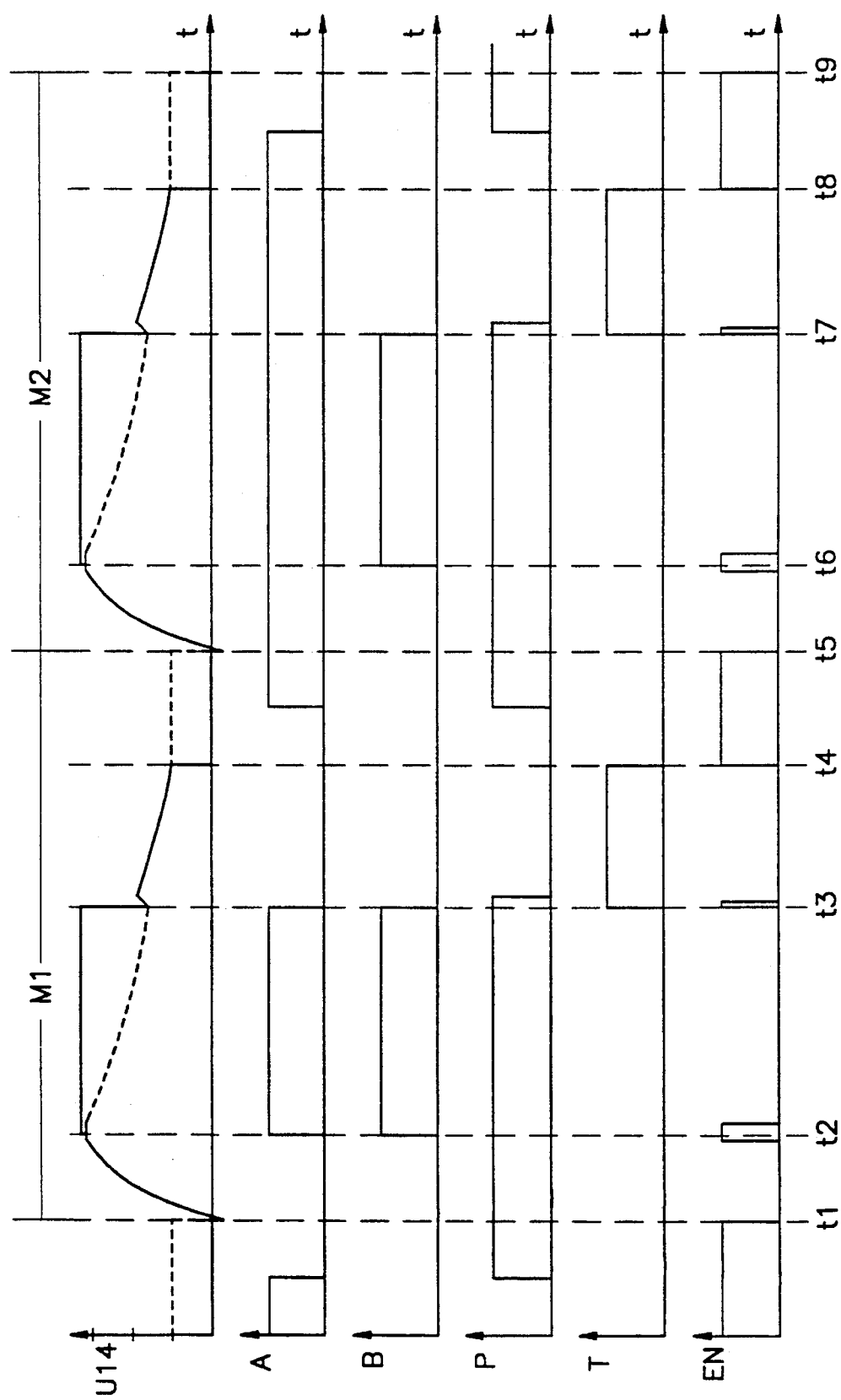
FIG. 2 is a diagram of the voltages and signals occurring within the circuit of FIG. 1.

The function of the circuit of FIG. 1 will be explained in further detail with reference to the timing diagram of FIG. 2. The control signals A, B, EN and P are produced in the microprocessor by a suitable program. The positions of the multiplexer as a function of the control signals A and B are shown in the following table.

| A | B | X | Y |
|---|---|---|---|
| 0 | 0 | X0 | Y0 |
| 1 | 1 | X3 | Y3 |
| 1 | 0 | X1 | Y1 |

At the time t1, the first measurement cycle M1 shown commences. The multiplexer is in the positions X0 and Y0, while a charge current is produced via the signal P and the diodes 21, 22, which current, however, begins to flow only when EN assumes the value of 0. The charge voltage of the capacitor 8, which corresponds, between t1 and t2, to the voltage U14 at the circuit point 14, increases up to the time t2, the charge current flowing to ground potential over the circuit point 14, the terminals X0 and X, the resistor 6, the capacitor 8, the resistor 7 and the terminals Y and Y0.

At the time t2, ⅔ of the voltage U is reached. Therefore, the output signal T of the threshold circuit jumps to 1. Thereupon, the microprocessor sets the control signals A and B at 1 so that the terminals X3 and Y3 are connected with the terminals X and Y, i.e. with the capacitor 8. EN is briefly set at 1, so that simultaneous connection of the terminals X0 and X3 and Y0 and Y3 respectively is prevented. During the following time until t3, the capacitor 8 is discharged over the resistance sensor 11 (dashed line), the speed of the discharge being dependent on the wetness. The voltage at the circuit point 14 remains at its maximum value during this time. After a predetermined constant time (t3–t2) the capacitor 8 is connected with ground and with the input 14 of the threshold circuit due to the fact that the control signals A and B drop again to 0. In this case also, the multiplexer 1 is switched to high resistance for a short time by EN=1.

Furthermore, slightly later, the voltage P is set at 0 so that the capacitor 8 is only briefly charged over the diodes 21, 22 and is then discharged over the measurement resistor 20 until a predetermined threshold value, namely ⅓ U, is dropped below at t4. As a result, the output signal T of the threshold circuit assumes the form shown in line T in FIG. 2, the duration of state 1 being a measure of the voltage on the capacitor at the time t3, and thus a measure of the resistance of the resistance sensor 11. The duration of this state is measured in the microprocessor 2 by means of a counter, the counter reading of which at the time t4 represents the measurement result.

During the following time interval between t4 and t5, the multiplexer 1 provides for high resistance (EN=1) so that the voltage U14 drops to 0 while the voltage on the capacitor 8 (shown in dashed line) remains practically constant. In this way, a preparation for the reversal of the polarity of the capacitor 8 is obtained and time created for a synchronizing of the microprocessor 2. The control signal A and the signal P are set at 1 during this period of time, so that the charging process can commence at the time t5 by the setting of the signal EN to zero. In this connection, to be sure, the multiplexer 1 is in the position X1, Y1, so that the capacitor 8 is charged with reverse polarity. At the time t6, the charged capacitor is then again connected to the resistance sensor 11 and discharged by the latter until the time t7. There then again takes place a discharge over the measurement resistor 20 until the threshold value of the threshold circuit is reached at the time t8, as a result of which the signal T again jumps from 1 to 0. The time between t8 and t7 is then again measured in the microprocessor. The second measurement cycle M2 is then at an end at the time t9.

In one circuit arrangement of the invention which has been reduced to practice, the following values were selected for the resistors designated with the same reference numerals, and for the capacitor 8:

| | | |
|---|---|---|
| $C8 = 0.1\ \mu F$ | $R6 = R7 = 221\ \Omega$ | $R9 = R10 = 4.75\ k\Omega$ |
| $R16 = R17 = 100\ k\Omega$ | $R18 = 57/6\ k\Omega$ | $R19 = 4.75\ k\Omega$ |
| $R20 = 26.7\ k\Omega.$ | | |

I claim:

1. A process for measuring the resistance of a resistance sensor in a succession of measurement cycles via a rate of change of the charge of a capacitor to be employed with a measurement circuit for energizing the resistance sensor; the process comprising the steps of:

charging the capacitor during a first time interval in a first measurement cycle;

discharging the capacitor partially through the resistance sensor during a second predetermined interval of time to obtain a remaining charge in the capacitor;

disconnecting the capacitor from the resistance sensor;

discharging the capacitor partially through a known resister during a third interval of time to obtain a predetermined value of capacitor voltage;

measuring the length of the third time interval, the length of the third time interval being a measure of the resistance of the resistance sensor; and varying the direction of a discharge current of the capacitor through the resistance of the sensor from measurement cycle to measurement cycle.

2. A circuit for measuring resistance of a resistance sensor comprising:

a source of charge/discharge current, a threshold circuit having an input terminal, the resistance sensor, and a capacitor;

a controllable two-pole multiple-switch multiplexer, the multiplexer having a pair of input terminals (X; Y) and two sets of output terminals (X0 to X3; Y0 to Y3) selectively connectable to the input terminals as a function of control signals applied to control terminals of the multiplexer; and wherein the input terminals X,Y are connected to the capacitor;

the resistance sensor is connected to the output terminals X3, Y3;

an input terminal of the threshold circuit is connected to an output terminal of the current source to enable a charging of the capacitor during a first time interval;

the input terminal of the threshold circuit and ground potential are connected respectively to the output terminals X1, Y1, with polarity opposite that of the second output terminals X0, Y0;

wherein the multiplexer is operative to connect the capacitor to the resistance sensor during a partial discharge of the capacitor during a second predetermined time interval, to disconnect the capacitor from the resistance sensor subsequent to the partial discharge, and to connect the capacitor to the threshold circuit for a partial discharge of the capacitor through a known resistance during a third interval of time, the duration of the third time interval being a measure of the resistance of the resistance sensor.

3. A process according to claim 1, wherein said changing step comprises steps of:

charging the capacitor by a defined amount of charging indicated by a measurement voltage; and measuring a time of the defined charging until a predetermined voltage is exceeded.

4. A process according to claim 1, wherein the resistance sensor in a wetness sensor, the process comprising a step of:

operating the circuit to apply voltage of alternating polarity to the resistance sensor for the discharge of the capacitor while maintaining freedom of electrolytic potential.

5. A process according to claim 1, further comprising a step of:

from measurement cycle to measurement cycle, connecting the capacitor with alternating polarity to a source of charge/discharge current and to an input of threshold circuit.

6. A circuit according to claim 2, further comprising:

a microprocessor, wherein control inputs of the multiplexer, the source of charge/discharge current, and an output of the threshold circuit are connected to terminals of the microprocessor.

7. A circuit according to claim 6, further comprising a second resistance sensor connected to the multiplexer output terminals X2, Y2.

8. A circuit according to claim 6, further comprising a reference resistor;

wherein output terminals X2, Y2 of the multiplexer are connected to the reference resistor for purposes of self-calibration.

9. A circuit according to claim 2, further comprising a reference resistor;

wherein output terminals X2, Y2 of the multiplexer are connected to the reference resistor for purposes of self-calibration.

10. A circuit according to claim 2, further comprising a second resistance sensor connected to the multiplexer output terminals X2, Y2.

* * * * *